Jan. 30, 1962 E. B. GRAVES Re. 25,118
X-RAY APPARATUS
Original Filed Nov. 26, 1957
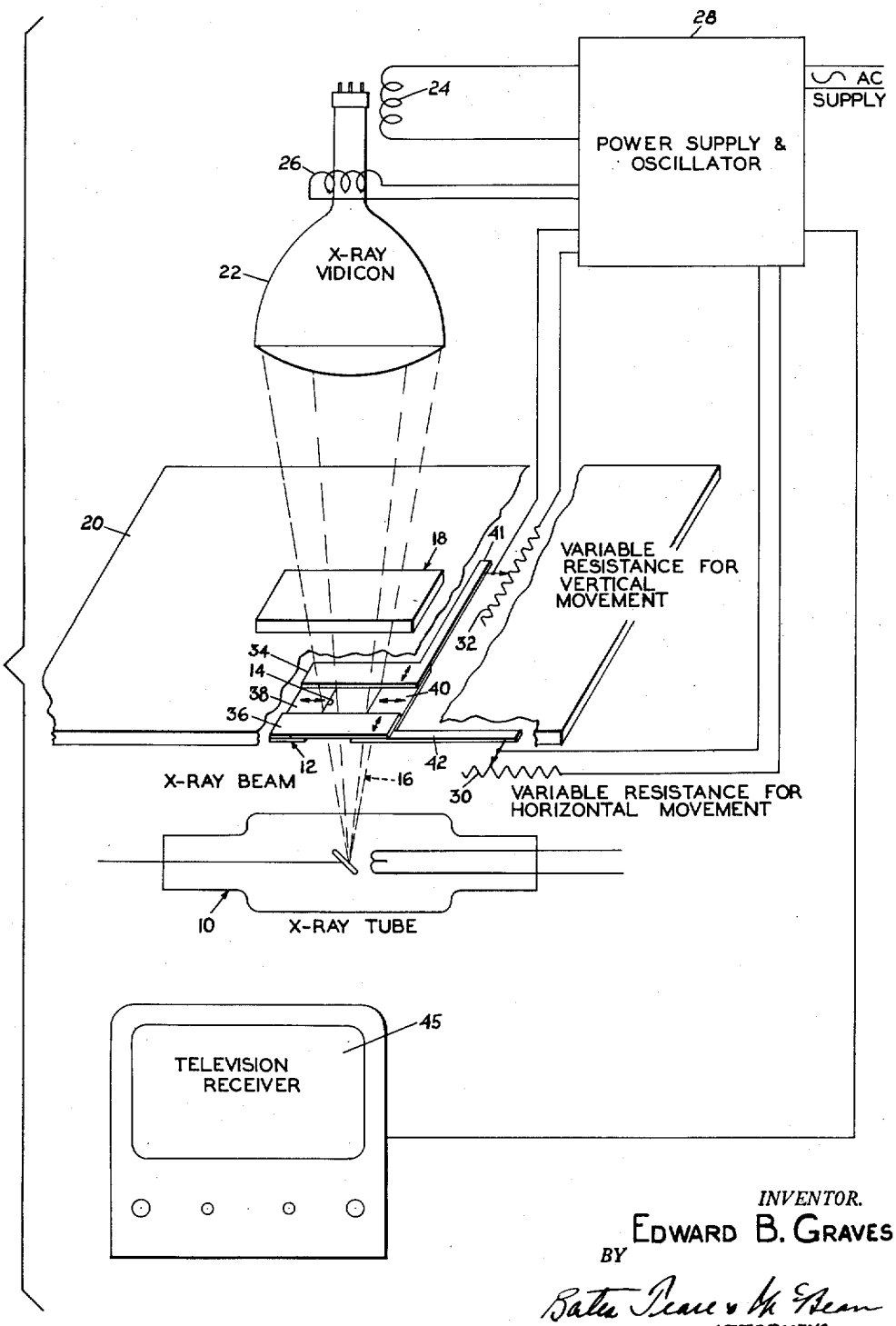
INVENTOR.
EDWARD B. GRAVES
BY
Bates Peace & Ashman
ATTORNEYS United States Patent Office Re. 25,118
Reissued Jan. 30, 1962

25,118
X-RAY APPARATUS

Edward B. Graves, South Euclid, Ohio, assignor to Picker X-Ray Corporation, Waite Manufacturing Div., Inc., Cleveland, Ohio, a corporation of Ohio Original No. 2,905,827, dated Sept. 22, 1959, Ser. No. 698,994, Nov. 26, 1957. Application for reissue Sept. 21, 1960, Ser. No. 57,599
8 Claims. (Cl. 250—93)

Matter enclosed in heavy brackets [ ] appears in the original patent but forms no part of this reissue specification; matter printed in italics indicates the additions made by reissue.

This invention relates in general to X-ray or fluoroscopy apparatus and to shutter mechanism in such apparatus as employed in X-ray examinations, and more particularly to such X-ray apparatus and shutter mechanism used in combination with control means and with X-ray stimulated mechanism, such as a photoconductive pick-up tube for furnishing a signal, in accordance with the viewing area of the part or object penetrated by the X-rays, which can then be transmitted to a picture producing device, such as a kinescope tube, to produce an effective picture of the portion of the object penetrated by the X-rays.

While the invention will be described and is shown in the accompanying drawing in combination with a photoconductive pick-up tube and a kinescope tube for receiving the signal from the photoconductive tube and producing a picture thereon, it will be understood that the X-ray apparatus and associated shutter mechanism and control means could be used in combination with other X-ray stimulated mechanism, and for control of the latter. For instance, the mechanism of the invention could be used for the effective control and coordination of an X-ray stimulated signal for transmission to mechanism such as tape equipment, for permanent recording of the signal and subsequent play-back.

The advantages associated with being able to produce an effective picture of the part or article irradiated by X-rays, or a permanent tape recording of a signal produced by such radiation, are obvious. The use of a photoconductive camera or pick-up tube or "Vidicon" as it is known in the art, with X-ray or fluoroscoping equipment, provides many advantages as compared to the use of an image amplifier tube, or image orthicon pick-up tube, as it is sometimes known, for accomplishing the same result. Some of the advantages are increased sensitivity, thus providing operation at lower light levels, decreased bulk and weight, and substantial simplification of mechanism. A photoconductive pick-up tube or "Vidicon" broadly comprises a glass envelope having a face with a specially prepared plate or photoconductive target on the inner side thereof. Many materials, such as selenium and sulphur, as well as the sulfides, selenides and oxides are known to be photoconductive, and when properly processed have been found suitable for pick-up tube plates or targets. The target plate or screen is adapted to be stimulated by a medium, such as light, X-rays or the like, from a source disposed exteriorly of the glass envelope and it has been found that the spectral response of the target plate is a function of the material used and the processing thereof. The rear-end of a photoconductive tube contains an electron gun consisting of a filament which furnishes the electrons, and deflecting means either electrostatically or magnetically actuated, which causes a focus beam of electrons to scan the aforesaid photoconductive layer or target plate. As the electron beam or pencil passes over the different areas of the target screen, more or less current will pass down the pencil depending upon whether the area scanned is light or dark. The current passing through the pencil then furnishes a signal which can be taken off the tube for further use on the aforementioned kinescope or television tube or on tape equipment or the like. Since the electron pencil as indicated above is caused to scan in two directions, vertically and horizontally, the height of the scan as well as the length of the scan can be controlled to cover any size or shape that is desired, by proper adjustment of voltages applied to the deflecting means of the photoconductive tube.

In the normal process of X-ray or fluoroscopy, the radiologist usually starts out with a relatively large field and then orients himself to bring the image down to the area in which he is most interested. The radiologist tries to keep the viewing area as small as possible, not only to reduce the amount of X-ray impinging upon the object being irradiated, which is very important in case the object comprises living matter, but also to reduce the "scatter" and improve the visual acuity of the resultant picture. The variation of the viewing area is accomplished in most X-ray or fluoroscopic equipment, by means of X-ray opaque shutter means, which can be actuated or moved to change the size of the aperture defined by the shutter means through which the X-rays pass into the object being irradiated.

Furthermore, the aforesaid photoconductive tube or "Vidicon" has the disadvantage of presenting a picture which is a series of black and white lines. Substantially half the scanned area results in black lines and half in white lines, and if the field has, for instance, 500 lines (which is generally the present scanning rate in television), it will be apparent that the width of the black lines, or signal voids, will be significant in the overall picture, and may possibly black out a vital point of interest in the object being X-ray examined. If, on the other hand, the scanning field is reduced in size, the thickness of both the black and white lines, constituting the picture on the kinescope, is reduced, and the potential area of black out of significant detail is minimized.

The above subject matter is generally known in the art. However, an arrangement for automatically controlling associated X-ray stimulated, sensing apparatus as for instance electrically varying the scan of an X-ray "Vidicon" tube, in coordination with the facility of varying the viewing area of the X-ray apparatus by means of the aforementioned shutter mechanism, provides unique advantages, especially in connection with the obtaining of clearer and sharper images or pictures for the radiologist.

The instant invention provides an X-ray apparatus including adjustable shutter mechanism and embodying control means which translates the opening and closing movement of the shutter mechanism to automatically control associated X-ray simulated sensing mechanisms in coordination with the aforesaid movement of the shutter mechanism. In the environmental embodiment of the invention shown, the X-ray apparatus which includes adjustable, X-ray opaque shutter mechanism, translates the opening and closing movement of the shutter to control automatically the voltage applied to the deflecting means of a photoconductive tube, and to vary automatically the scan of the tube in coordination with movement of the shutter, thereby producing much clearer and sharper images on a kinescope which represents the final viewing screen for the radiologist.

Accordingly, an object of the invention is to provide an X-ray or fluoroscopic apparatus which includes an adjustable shutter mechanism, and control means associated with such mechanism, for controlling and regulating, in automatic coordination with the movement of the shutter mechanism, an associated X-ray stimulated device.

A further object of the invention is to provide an X-ray or fluoroscopic mechanism, including a photoconductive tube in which means are provided to automatically vary the scan of the tube in coordination with the movement of the shutter of the X-ray or fluoroscopic mechanism, to thus keep the scan field in step with the shutter opening.

Another object of the invention is to provide an X-ray apparatus of the latter mentioned type in combination with picture producing means, such as a kinescope tube, whereby the picture produced by the picture producing means from the signal of the photoconductive tube is clear and sharp in detail.

A still further object of the invention is to provide an X-ray or fluoroscopic mechanism including a photoconductive tube in which the movement of the shutter mechanism of the X-ray apparatus is utilized to vary the resistance of suitable potentiometers controlling the horizontal and vertical sweep circuits of the photoconductive tube, to vary automatically the scan of the photoconductive tube in coordination with the movement of the shutter mechanism.

Other features that are advantages of the invention will be apparent from the following description taken in conjunction with the accompanying drawings wherein—

The FIGURE in the drawing is a generally diagrammatic, partly cut away view of an X-ray apparatus disposed in an organized system for carrying out the instant invention.

Referring to the drawing there is diagrammatically illustrated a directed source of X-ray, represented by a conventional X-ray tube 10, an X-ray opaque shutter mechanism 12 defining an aperture 14 through which the X-ray beam 16 passes to irradiate the object 18 which is the subject of observation. The object 18 in the embodiment shown is supported on a table top 20. After passing through object 18, the X-ray beam impinges on the photoconductive tube or X-ray "Vidicon" tube 22 and stimulates the aforementioned target plate of the photoconductive tube. The target plate is scanned by the electron beam produced by the electron gun in the rear of the photoconductive tube, as aforediscussed, thereby producing a signal which is adapted to be transmitted to suitable receiving mechanism such as a kinescope tube, tape equipment etc., for further processing. The electron beam of the photoconductive tube is deflected across the target plate by deflecting coils 24 and 26 which are connected into conventional power supply and oscillator circuit 28 for supplying the sweep potentials to coils 24 and 26. Connected in the power supply and oscillator circuit and to the deflecting coils 24 and 26 are suitable potentiometers 30 and 32 which are of conventional character and which are adapted to vary the sweep or scan of the photoconductive tube 22, as will hereinafter be more thoroughly discussed.

The aforediscussed shutter means 12 is mounted intermediate the X-ray tube 10 and the object 18 being examined, and defines aperture 14 through which the directed X-rays emanating from the X-ray source 10 will pass to the object 18. The shutter may comprise a pair of plates 34 and 36 of X-ray opaque materials such as lead, and a second pair of similar plates 38 and 40 overlapping the first pair and generally positioned at right angles thereto. By moving the X-ray opaque plates relative to one another, the size of aperture 14 can be varied, thus varying the cross sectional area of the X-ray beam irradiating object 18, and the resultant viewing area thereof. Actuation or movement of the shutter mechanism can be accomplished in any conventional manner, such as by means of linkages, gearing etc. Arrangements for such movement of a shutter apparatus in X-ray or fluoroscopy equipment are well known in the art, and accordingly will not be discussed in detail here. One such arrangement which could be utilized in the above purposes is shown and described in U.S. Patent No. 1,953,497, issued April 3, 1934, to A. C. Nelson. One pair, 34—36, of the lead shutter plates are operatively connected to the potentiometer 32, as for instance by arm portion 41 illustrated in the diagrammatic embodiment of the invention shown, while another pair, 38—40, of the plates are operatively connected, as for instance by arm portion 42, to potentiometer 30. Thus, upon relative movement of plates 34—36 with respect to one another the resistance of potentiometer 32 will be automatically varied in accordance with such movement of the shutter plates, thus varying the sweep voltage applied by vertical deflection coil 26 to the deflecting means of photoconductive tube 22, and thereby varying the vertical scan or sweep of the electron beam. Likewise upon relative movement of plates 38—40, the resistance of potentiometer 30 is automatically changed in accordance with such movement, thus varying the horizontal sweep or scan of tube 22. It will be seen therefore that the scan or sweep of the photoconductive pick-up tube is automatically coordinated with, and kept in step with, the movement of the shutter mechanism of the X-ray apparatus, by the control potentiometers 30 and 32 thus resulting in a much clearer and sharper picture on the picture producing device or kinescope tube 45 which picks up the signal, as afore stated, emanating from the photoconductive tube 22. These same controls generally represented in the embodiment of the invention shown, by the movable arm portions 41 and 42 of the shutter mechanism in combination with the potentiometers 32 and 30, can be used to adjust the final image size appearing on the kinescope. The picture on the kinescope, which represents the final viewing screen for the radiologist, can either be left in the size as produced by the kinescope, or can be enlarged with suitable sweep controls of conventional character on the kinescope or television receiver itself.

From the foregoing description and accompanying drawings, it will be understood that the invention provides a novel X-ray or fluoroscopic apparatus which includes adjustable shutter mechanism and control means operatively connected to the shutter mechanism for automatically regulating an associated X-ray stimulated device in positive coordination with the adjusting movement of the shutter mechanism. The invention also provides an apparatus of the above mentioned general type in which the X-ray stimulated device comprises a photoconductive tube for emitting a signal corresponding to the object being irradiated by the X-ray, and which is automatically coordinated with the viewing area established by the shutter mechanism of the X-ray apparatus, thereby resulting in a clearer and sharper picture of the irradiated portion of the object, when the signal is transmitted to a picture producing device such as a kinescope tube for visual reproduction. Furthermore, the invention provides an X-ray apparatus of the latter mentioned type in which the controls that move or actuate the shutter mechanism of the apparatus also control the size of the final image produced on the kinescope tube by automatically coordinating the sweep or scan of the photoconductive tube with the movement of the shutter mechanism.

The terms and expressions which have been employed are used as terms of description and not of limitation and there is no intention in the use of such terms and expressions of excluding any equivalents of the features shown and described or portions thereof, but it is recognized that various modifications are possible within the scope of the invention claimed.

I claim:

1. In combination, a source of X-rays positioned to direct a beam of X-rays at an object to be irradiated, an X-ray stimulated device having a target area positioned to intercept the modulated X-rays passing through the object, adjustably X-ray opaque shutter means disposed in the path of the X-rays between the source and the object to control the width of the X-ray beam and thereby the size of the stimulated target area, means for scanning the target area and translating the X-ray stimulation thereon into a corresponding signal, means for adjusting said scanning means to conform to the area of X-ray stimulation on the target area, and means coacting between said adjustable shutter means and said scan adjusting means to automatically coordinate the scan with the stimulated target area.

2. The combination of claim 1 wherein said scan adjusting means is controlled by an electrical signal and wherein said coordinating means includes a potentiometer operably coupled between the adjustable shutter means and the scan adjusting means to convert the shutter adjustment into a corresponding scan control signal.

3. In combination, a source of X-rays positioned to direct beam of X-rays at an object to be irradiated, an X-ray stimulated device having a target area positioned to intercept the modulated X-rays passing through the object, adjustable X-ray opaque shutter means disposed in the path of the X-rays between the source and the object to control the width of the X-ray beam and thereby the size of the stimulated target area, means for scanning the target area and translating the X-ray stimulation thereon into a corresponding signal, means for converting said signal into a visual image corresponding to the modulated stimulation of the target area, means for adjusting said scanning means to conform to the area of X-ray stimulation on the target area, and means coacting between said adjustable shutter means and said scan adjusting means to automatically coordinate the scan with the stimulated area of the target.

4. In combination, an X-ray source, adjustable X-ray opaque shutter means disposed in the path of the X-rays and between said source and a subject to be irradiated, said shutter means comprising at least two pairs of X-ray opaque plate members, said pairs being disposed in overlapped and substantially right-angled relationship with respect to one another to define an aperture therebetween through which the X-rays travel to the subject, the plates of each of said pairs being movable relative to one another to thereby adjust the size of said aperture, an X-ray stimulated device having a target area positioned to intercept the modulated X-rays passing through the subject and be stimulated thereby, said device having means including an electron beam for scanning the target area and translating the X-ray stimulation on such target area into a corresponding video control signal, electrically controlled means for adjusting said scanning means to conform to the area of X-ray stimulation on the target area, means coacting between said adjustable shutter means and said scan adjusting means to automatically coordinate the scan with the stimulated portion of the target area responsive to adjustment of said shutter means, said coordinating means including a pair of potentiometers, each of said potentiometers being coupled for adjustment by a respective one of said pairs of plates of said shutter means and being electrically coupled to said scan adjusting means, one of said potentiometers being operable to vary the vertical scan of said scanning means and the other of said potentiometers being operable to vary the horizontal scan of said scanning means in accordance with movement of the respective of said pairs of plates of said shutter means.

*5. In a mechanism including a support for an object to be studied, a source of X-ray energy positioned on one side of the support and a movable diaphragm positioned between the source of X-ray energy and the support, said diaphragm being adjustably positionable to delimit an energy beam of a selected size, the combination of, a pick-up tube having an input screen positioned on a side of the support opposite the source and positioned for activation by an object affected flow of energy initiated by said source, a picture tube having a picture producing screen, electronic circuit means connected to the tubes to transmit output of the pickup tube to the picture tube, and control means actuated by said diaphragm and electrically connected to said circuit means to vary the magnification and clarity of a picture on said picture producing screen in response to adjustment of the diaphragm while maintaining the area essentially constant.*

*6. The device of claim 5 wherein one of said tubes includes a scan means to scan the screen of said one tube and said control means is connected to the scan means to vary the scan in proportion to adjustment of said diaphragm.*

*7. The device of claim 5 wherein the control means is a variable potentiometer.*

*8. In a mechanism for producing an X-ray stimulated image of an object the combination of, a support for an object to be examined, an X-ray tube positioned on one side of said support, adjustable diaphragm means between said tube and said support for delimiting a beam of X-rays for impingement against such object, a pick-up tube including a screen for producing an electronically detectable image and scan means for scanning the image, means including at least said screen for converting the beam of X-rays into such electronically detectable image on said screen, a picture tube, electronic circuit means connecting said tubes together to transmit a scan means emitted impulse to said picture tube and thereby produce an optically visible picture and means connecting the diaphragm means to the circuit means to vary the magnification and clarity of the produced picture in proportion to adjustments of the diaphragm means while maintaining the area of the produced picture substantially constant.*

References Cited in the file of this patent or the original patent

UNITED STATES PATENTS

| | | |
|---|---|---|
| 2,788,453 | Lusted | Apr. 9, 1957 |
| 2,837,657 | Craig et al. | June 3, 1958 |

OTHER REFERENCES

Moon: "Amplifying and Intensifying the Fluoroscopic Image by Means of a Scanning X-Ray Tube," Science, vol. 112, Oct. 6, 1950, pages 389 to 395.